US00PP20437P2

(12) United States Plant Patent
Korban et al.

(10) Patent No.: US PP20,437 P2
(45) Date of Patent: Oct. 20, 2009

(54) APPLE TREE NAMED 'CO-OP 31'

(50) Latin Name: *Malus×domestica*
Varietal Denomination: Co-op 31

(75) Inventors: Schuyler S. Korban, Champaign, IL (US); Joseph C. Goffreda, Millstone, NJ (US); Jules Janick, West Lafayette, IN (US)

(73) Assignees: The Board of Trustees of the University of Illinois, Urbana, IL (US); Rutgers, The State University of New Jersey, New Brunswick, NJ (US); Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 12/082,499

(22) Filed: Apr. 11, 2008

(51) Int. Cl.
*A01H 5/00* (2006.01)

(52) U.S. Cl. ..... Plt./161

(58) Field of Classification Search ..... Plt./161
See application file for complete search history.

(56) References Cited

OTHER PUBLICATIONS

Rosenberger, D. A. An update on scab-resistant cultivars and advanced selections for consideration in new plantings. UVM Apple Orchard, SRC Update, written 1995 and modified 2000 [online]. Retrieved from the Internet: <http://orchard.uvm.edu/sap/srcupdate.html> 9 pp.*

Sandskar et al. Classification of apple scab resistance in two assortment orchards. Genetic Resources and Crop Evolution 51: 197-203, 2004.*

* cited by examiner

*Primary Examiner*—June Hwu
(74) *Attorney, Agent, or Firm*—Klarquist Sparkman, LLP

(57) ABSTRACT

A new apple variety distinguished by the following unique combination of characteristics: It is field-immune to apple scab disease, has good resistance to the bacterial disease fire blight, and moderate resistance to the fungal disease powdery mildew. This new apple is relatively late ripening. It has medium-large fruit size, red colored fruit, with excellent flavor (full favored, fruity, sweet, mild-subacid). The fruit hangs well on the tree, even after ripening. The tree is highly productive on an annual basis.

3 Drawing Sheets

Latin name of the genus and species of the plant claimed: *Malus×domestica.*

Variety denomination: 'Co-op 31'.

BACKGROUND OF THE INVENTION

The present invention relates to a new and distinct variety of apple tree named 'Co-op 31'. Our new tree resulted from a planned hybridization program and is a selection from crossing Rock 41-12 (unpatented) as the seed parent with PRI 841-103 (unpatented) as the pollen parent. The original cross was performed in 1968 in Illinois. The resulting tree was selected when growing in a cultivated area at Urbana, Ill.

BRIEF SUMMARY OF THE INVENTION

The 'Co-op 31' variety is distinguished from other apple varieties due to the following unique combination of characteristics: field-immune to apple scab disease, good resistance to the bacterial disease fire blight, and moderate resistance to the fingal disease powdery mildew. This new apple is relatively late ripening. It has medium-large fruit size, red colored fruit, with excellent flavor (full favored, fruity, sweet, mild-subacid). The fruit hangs well on the tree, even after ripening. The tree is highly productive on an annual basis.

'Co-op 31' is a high yielding, late season apple. Fruit is firm, crisp, with outstanding fruit flavor, and a very good storage life. Fruit of 'Co-op 31' is round in shape, and it is 100% dark red in color. 'Co-op 31' is superior to either parent in fruit quality and disease resistance. Fruit of the parent 'Rock 41-12' is only 50% red with good quality; while, fruit of the other parent 'PRI 841-103' is round-conic in shape, 90% medium red color, and has only fair eating quality.

The 'Co-op 31' tree is moderately vigorous, semi-spreading, with a desirable bearing habit (fruit is well-distributed throughout the canopy), and crops heavily on an annual basis. In addition, the tree has sturdy wood with no blindwood. This apple has immunity to apple scab (*Venturia inaequalis* Cke. Wint) and good resistance to the bacterial disease fire blight (incited by *Erwinia amylovora* (Burr.) Winslow) and moderate resistance to the fungal disease powdery mildew (incited by *Podosphaera leucotricha* (Ell. & Ev.) Salm.).

Asexual reproduction of this new variety by grafting and budding onto rootstock Malling 7 (unpatented) shows that the foregoing characteristics come true to form, are firmly fixed, and are established and transmitted through succeeding propagations. 'Co-op 31' has been asexually reproduced in Urbana, Ill.; West Lafayette, Ind.; and Cream Ridge, N.J.

The following detailed description concerns the original tree, discovered in 1968, and progeny first asexually propagated in 1970. The original tree and progeny have been observed growing in a cultivated area in Urbana, Ill.

Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart.

Figure 1:
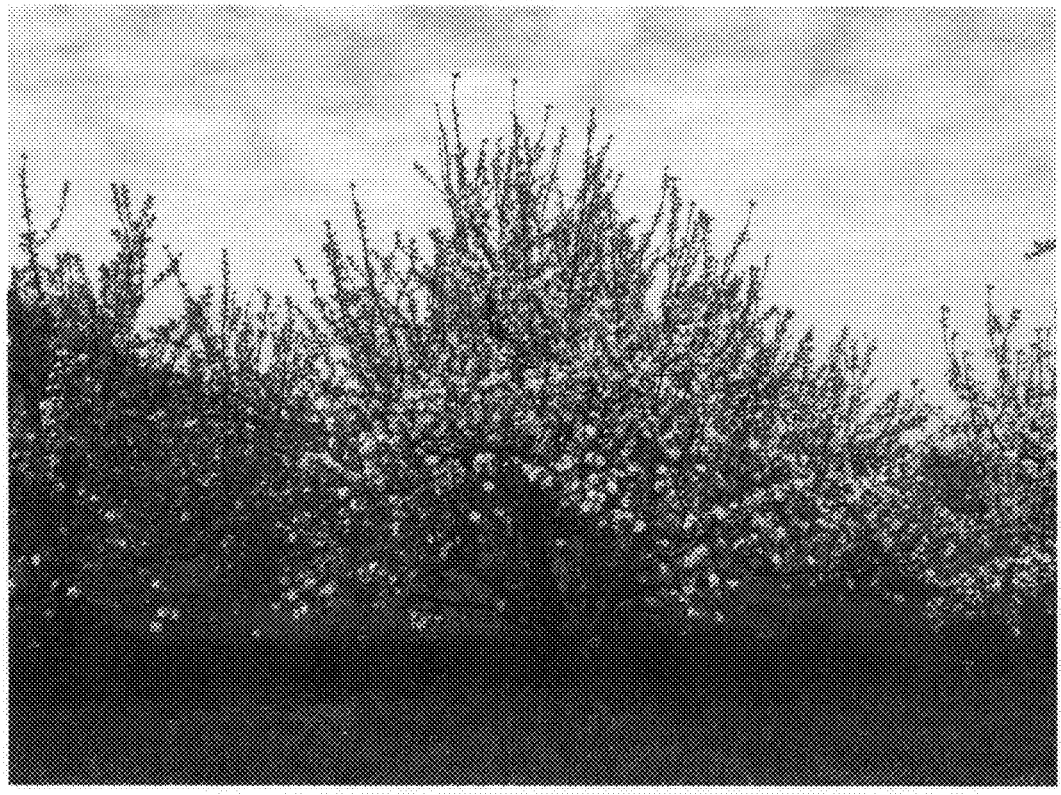
FIG. 1 is a photograph showing the whole 'Co-op 31' variety when in bloom.
Figure 2:
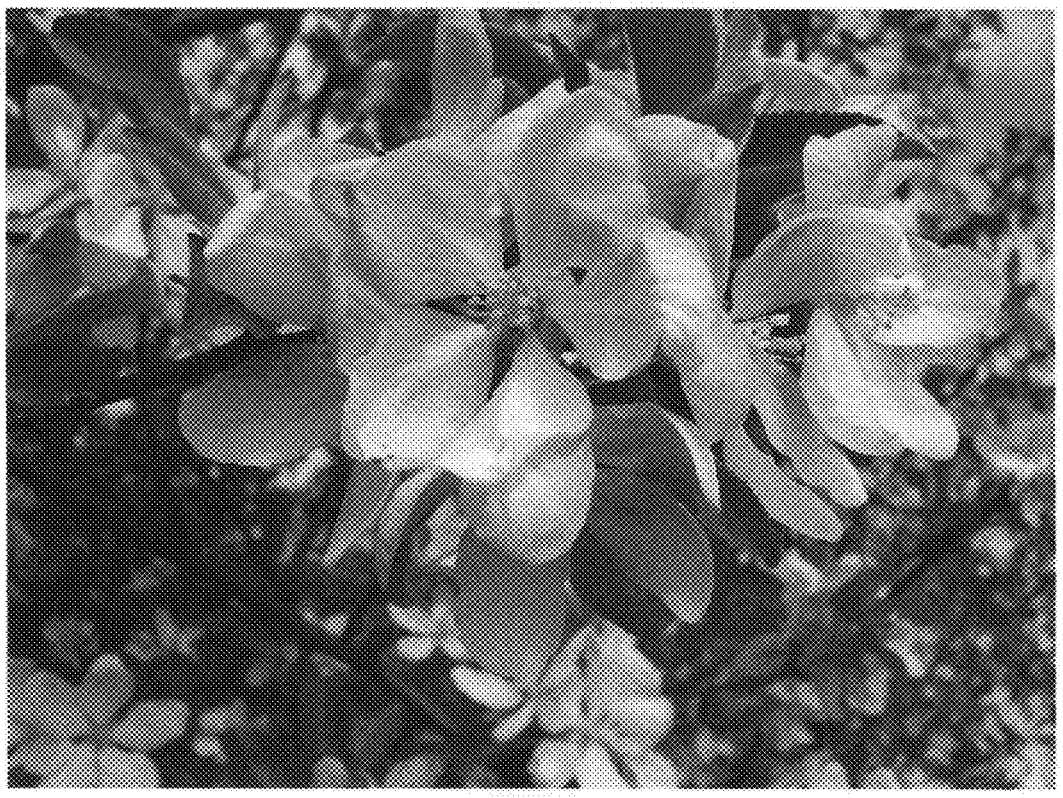
FIG. 2 is a photograph showing a close-up of 'Co-op 31' flowers.
Figure 3:
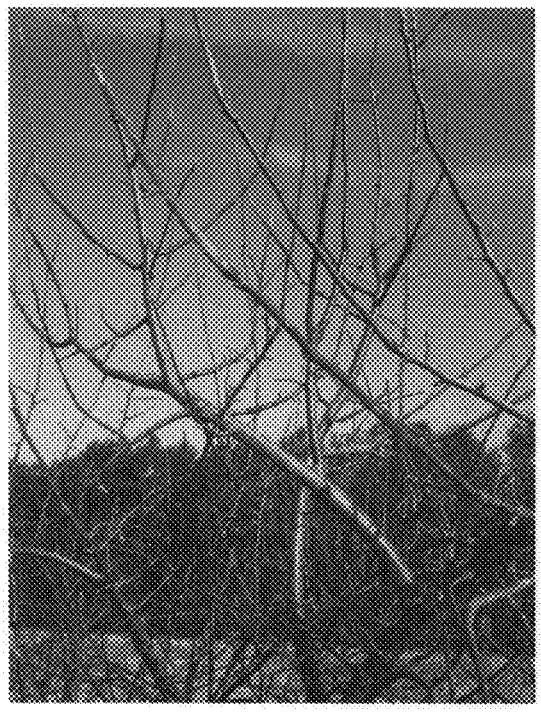
FIG. 3 is a photograph showing the 'Co-op 31' tree when not in bloom.
Figure 4:
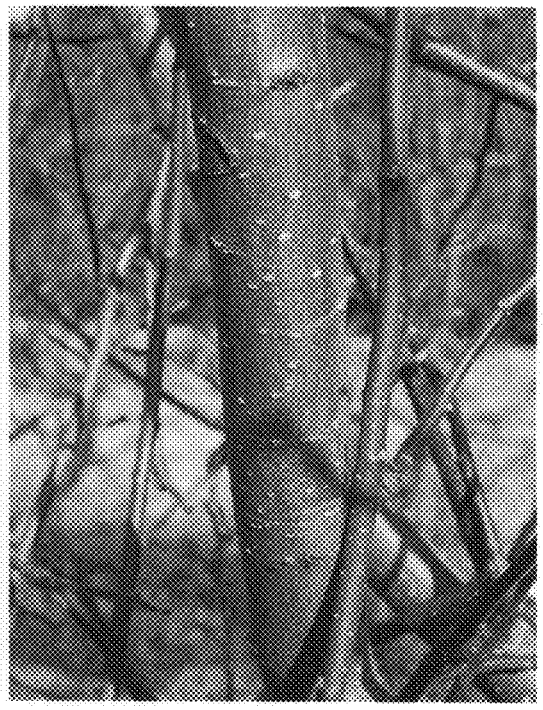
FIG. 4 is a photograph showing the 'Co-op 31' bark.
Figure 5:
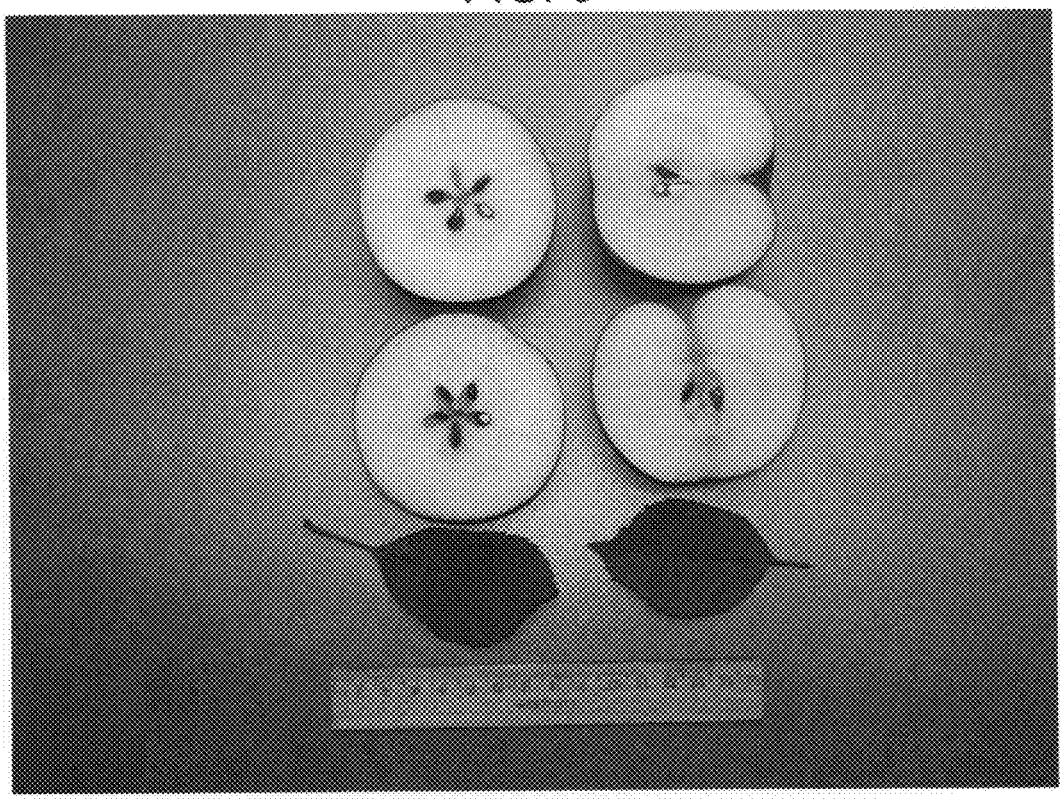
FIG. 5 is a photograph showing the 'Co-op 31' cut fruit and leaves.
Figure 6:
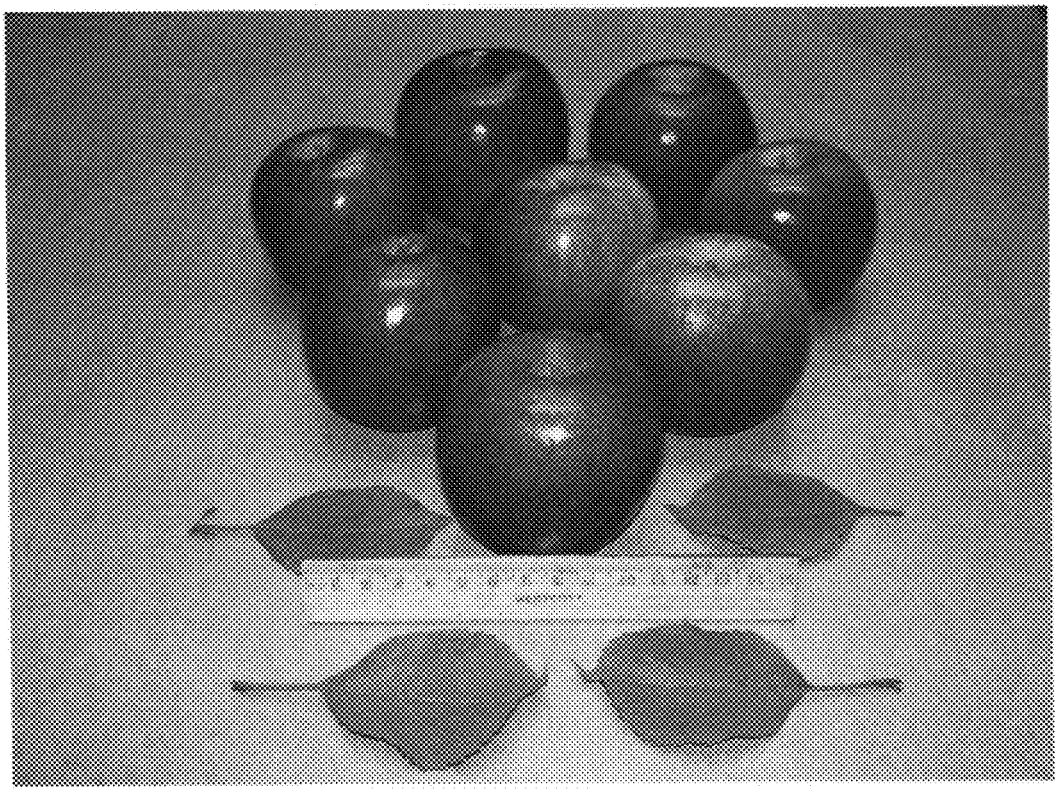
FIG. 6 is a photograph showing the 'Co-op 31' whole fruit and leaves.

The colors of an illustration of this type may vary with lighting and other conditions under which conditions and, therefore, color characteristics of this new variety should be determined with reference to the observations described herein, rather than from these illustrations alone.

DETAILED DESCRIPTION

BOTANICAL

The following detailed description of the 'Co-op 31' variety is based on observations of asexually reproduced progeny. The observed trees were 8 years of age and growing on Malling 7 (unpatented) rootstock at Urbana, Ill.

Scientific name: *Malus×domestica* 'Co-op 31'.

Parentage:

*Seed parent.*—Rock 41-12.

*Pollen parent.*—PRI 841-103.

Tree:

*Vigor.*—Moderate.

*Overall shape.*—Semi-spreading.

*Height.*—About 10 feet.

*Width.*—Overall spread of about 5½ feet.

*Trunk.*—2¼".

*Trunk bark texture.*—Smooth.

*Trunk bark color.*—Greyed Orange (RHS 174A).

*Patches or other markings.*—Trunk has tan lenticels that are linear (2.5 mm in length), and sometimes protruding Orange-white in color (RHS 159C).

*Primary branches.*—Similar in color and surface to trunk.

*Branch angle.*—45–90°.

*Branch color.*—One-year old branches are Greyed purple (RHS 183A) in color, while two-year old branches are Greyed purple (RHS 183B) in color.

*Branch pubescence.*—None.

*Branch lenticels.*—High-density, approximately ~17 per square inch; typical examples of which measured about 2.5 mm in length; Orange-white (RHS 159C) in color.

*Internodes.*—Average internode length is about ¾ inch on a one-year old shoot.

*Bearing.*—Standard.

*Disease resistance.*—Field immune to apple scab (*Venturia inaequalis* (Cke.) Wint.). Based on observations in the field, it has good resistance to the bacterial disease fire blight (incited by *Erwinia amylovora* (Burr.) Winslow), and moderate resistance to the fungal disease powdery mildew (incited by *Podosphaera leucotoricha* (Ell. & Ev.) Salm.). It also has moderately resistant to cedar apple rust (incited by *Gymnosporangium juniperi-virginianae* (Schw.)).

Leaves: Leaves are simple, mostly entire, ovate in shape, tip acuminate, base obtuse, and margins serrate

*Texture.*—Upper surface is glabrous; while, lower surface is slightly pubescent.

*Sheen.*—Slight. Length to Width ratio is ~1.62.

*Mature leaf blade.*—Average length is 7.2 cm and average width is 3.8 cm.

*Thickness.*—About 0.5 mm.

*Petiole: About* ¼ inches long; about 1 mm in diameter. Slightly pubescent, average length of 3 cm and 1 mm in diameter; yellow-green (RHS 146D).

*Margin.*—Serrate.

*Tip shape.*—Acuminate.

*Leaf color.*—Young: Upper and lower leaf surface: Green (RHS 137C).

*Leaf color.*—Mature.

Upper and lower leaf surface.—Green (RHS 137B). Upper surface glabrous, lower surface slightly pubescent. The length, width, thickness and other measurements were obtained from observations of ten typical leaves in August 2006 and August 2007.

Flowers:

*Size.*—4 cm to 4.6 cm in diameter.

*Color.*—Tight bud: Greyed-purple (RHS 186A); balloon stage: Greyed-purple (RHS 186D); Fully open — Red (RHS 56D) with more pink along veins of pedicel — Red-purple (RHS 70C) Unopened bud: Greyed-purple (RHS 186A). Opened flower: Red (RHS 56D) Petals are single (5 petals), independent and 4.0–4.6 cm in diameter when fully expanded.

*Bloom season.*—Mid-season; full bloom observed on Apr. 21, 2006.

Fruit: (Observations from a limited number of typical fruit in the orchard in Urbana, Ill.)

*Size.*—6 cm to 6.5 cm in diameter and fruit length (from basin to cavity) is 6.0–6.3 cm.

*Form.*—Round-oblong.

*Cavity.*—Acute, medium (1 cm), narrow (1 cm to 1.5 cm), with russet surface.

*Basin.*—About medium-wide (1.5 cm to 1.8 cm in width) with rounded sides.

*Stem.*—1 mm to 2 mm in width, and 0.5–0.8 cm in length.

*Color.*—Overcolor 100% Greyed purple (RHS 185A), washed/stippled with small yet conspicuous tan lenticels. Undercolor: green yellow.

*Pedicel.*—0.5 cm to 0.8 cm in length, short, not flexible (1 mm to 2 mm in width). Weight of 10 fruits is 4.4 lbs (i.e., weight of a single fruit is 0.44 lbs.).

*Flesh color.*—Yellow (RHS 158A). Flesh is crispy, juicy.

*Skin.*—Medium, slightly-glossy.

*Calyx.*—Persistent, narrowly lanceolate.

*Calyx tube.*—Conical shaped.

*Carpels.*—Round, ridged. Moderately conspicuous lenticels; tan color (RHS 159B); 10 lenticels per $cm^2$; average size 0.8 mm in diameter. Fruit overcolor almost 100% Red (RHS 185A) with no greasiness of skin. Cavity is acute, medium (1.0 cm), narrow (1.0–1.5 cm), with russet surface. Basin is medium-wide (1.5–1.8 cm in width), with rounded sides. Locules are closed, and seeds adhere to carpel wall.

*Seeds.*—Full complement, acute, non-tufted (5 mm in length and 3 mm across); Greyed Red (RHS 178B).

*Texture.*—Medium, firm, crisp, and breaking.

*Quality.*—Full flavored, fruity, sweet, mild-subacid, excellent. Ripening date in Urbana, Ill. (Oct. 10), heavy annual cropping Fruit properties at maturity (based on 10 fruits tested in Urbana, Ill.).

*Fruit production.*—Being picking on Oct. 8 till October 20 in Urbana, Ill.

*Firmness.*—21.9 lb.

*Soluble solids.*—12.75%.

*Juice pH.*—3.34. Starch index (on a scale of 1–9, 1 very ripe and 9 immature): 6.27 Fruit hangs well on the tree for another 2 weeks without dropping. Fruit is well distributed over the tree.

*Storage.*—Fruit remains fresh at room temperature for 30 days, and can be stored up to 7 months in cold storage (34° F.).

*Usage.*—Fresh eating and for processing (pies, juice, etc.).

We claim:

1. A new and distinct variety of apple tree, substantially as herein shown and described.

* * * * *

UNITED STATES PATENT AND TRADEMARK OFFICE

CERTIFICATE OF CORRECTION

PATENT NO. : PP 20,437 P2
APPLICATION NO. : 12/082499
DATED : October 20, 2009
INVENTOR(S) : Korban et al.

It is certified that error appears in the above-identified patent and that said Letters Patent is hereby corrected as shown below:

Column 1, line 5, add the following heading and paragraph:

ACKNOWLEDGMENT OF GOVERNMENT SUPPORT

This invention was made with government support under Grant No. IND011814R awarded by USDA/CSREES. The government has certain rights in the invention.

Signed and Sealed this

Thirtieth Day of March, 2010

David J. Kappos

David J. Kappos
*Director of the United States Patent and Trademark Office*